United States Patent
Martinez Ferreira et al.

(10) Patent No.: US 10,039,506 B2
(45) Date of Patent: Aug. 7, 2018

(54) METHOD FOR MOVING A MOTORIZED TABLE AND ASSOCIATED MEDICAL IMAGING SYSTEM

(71) Applicant: General Electric Company, Schenectady, NY (US)

(72) Inventors: Carlos Martinez Ferreira, Paris (FR); Omar Al Assad, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 70 days.

(21) Appl. No.: 14/647,643

(22) PCT Filed: Nov. 26, 2013

(86) PCT No.: PCT/US2013/071938
§ 371 (c)(1),
(2) Date: May 27, 2015

(87) PCT Pub. No.: WO2014/085418
PCT Pub. Date: Jun. 5, 2014

(65) Prior Publication Data
US 2015/0320382 A1    Nov. 12, 2015

(30) Foreign Application Priority Data

Nov. 27, 2012 (FR) .................... 12 61298

(51) Int. Cl.
*A61B 6/04*     (2006.01)
*H05G 1/52*     (2006.01)
(Continued)

(52) U.S. Cl.
CPC ............ *A61B 6/0457* (2013.01); *A61B 6/102* (2013.01); *A61B 6/542* (2013.01); *A61B 6/547* (2013.01);
(Continued)

(58) Field of Classification Search
CPC ......... A61B 6/0457; A61B 6/10; A61B 6/102; A61B 6/481; A61B 6/542; A61B 6/547;
(Continued)

(56) References Cited

U.S. PATENT DOCUMENTS 5,402,462 A    3/1995    Nobuta
5,825,843 A *  10/1998   Kobayashi ............. A61B 6/102
                                                              378/20
(Continued)

FOREIGN PATENT DOCUMENTS

EP    2380496 A1    10/2011
JP    S63234948 A    9/1988
(Continued)

OTHER PUBLICATIONS

Unofficial English Translation of French Search Report and Written Opinion issued in connection with FR Application No. 1261298 dated Aug. 29, 2013.
(Continued)

*Primary Examiner* — Irakli Kiknadze

(57) ABSTRACT

A method for moving a motorized table designed to receive a patient in a medical imaging system comprising a radiation detector capable of detecting a beam of radiation emitted by a radiation source, the method comprising generating a signal that indicates a movement of the motorized table in the plane of the motorized table causing or tending to cause said beam to at least partially or completely leave an area predefined by the user of the medical imaging system.

11 Claims, 2 Drawing Sheets

(51) Int. Cl.
*H05G 1/00* (2006.01)
*A61B 6/10* (2006.01)
*A61B 6/00* (2006.01)

(52) U.S. Cl.
CPC .............. *A61B 6/586* (2013.01); *A61B 6/10* (2013.01); *A61B 6/481* (2013.01); *A61B 6/548* (2013.01)

(58) Field of Classification Search
CPC ......... A61B 6/548; A61B 6/586; A61B 34/70; A61B 17/0218; A61B 17/3421; A61B 17/3423; A61B 17/3474; A61B 2017/00477; A61B 2017/3445; A61B 2017/3447; A61B 2034/302; A61B 2034/306; A61B 2090/5025; A61B 34/00; A61B 34/30; A61B 34/35; A61B 34/37; A61N 2005/1087; A61N 5/10; A61N 5/1049; A61N 5/1067; A61N 2005/1061; A61N 2005/1097; A61N 5/107; A61N 5/1077; A61N 5/1081; A61N 5/1043; A61N 5/1064; A61N 5/1082; A61N 5/1048; A61N 5/1037; A61N 5/1039; A61N 2005/0641
USPC ................. 378/4, 8, 15, 20, 95, 114, 209; 250/363.02, 363.05, 363.08
See application file for complete search history.

(56) References Cited

U.S. PATENT DOCUMENTS

| | | | |
|---|---|---|---|
| 5,878,112 A | 3/1999 | Koertge | |
| 5,949,811 A * | 9/1999 | Baba | A61B 6/4225 378/108 |
| 6,045,262 A * | 4/2000 | Igeta | A61B 6/0457 318/649 |
| 6,917,666 B2 * | 7/2005 | Wollenweber | A61B 6/04 378/20 |
| 7,623,623 B2 * | 11/2009 | Raanes | A61N 5/1049 378/205 |
| 8,280,492 B2 | 10/2012 | Niethammer | |
| 2006/0018431 A1 * | 1/2006 | Kanemitsu | A61B 6/105 378/117 |
| 2007/0129486 A1 | 6/2007 | Klein et al. | |
| 2007/0129846 A1 | 6/2007 | Birkenbach et al. | |
| 2009/0022275 A1 | 1/2009 | Grebner et al. | |
| 2009/0253109 A1 | 10/2009 | Anvari et al. | |
| 2010/0008475 A1 * | 1/2010 | Maschke | A61B 5/06 378/209 |
| 2011/0317815 A1 * | 12/2011 | Bernhardt | A61B 6/542 378/98.5 |
| 2012/0106708 A1 | 5/2012 | Trousset et al. | |
| 2013/0077744 A1 * | 3/2013 | Kamiya | A61B 6/5241 378/62 |

FOREIGN PATENT DOCUMENTS

| | | |
|---|---|---|
| JP | 08336526 A | 12/1996 |
| JP | 10118060 A | 5/1998 |
| JP | 11318877 A | 11/1999 |
| JP | 2000316840 A | 11/2000 |
| JP | 2007267783 A | 10/2007 |
| JP | 2011004966 A | 1/2011 |
| WO | 2012120477 A2 | 9/2012 |

OTHER PUBLICATIONS

International Search Report dated Apr. 14, 2014 which was issued in connection with PCT Patent Application No. PCT/US2013/071938 which was filed on Nov. 26, 2013.

Unofficial English translation of Japanese Office Action issued in connection with corresponding JP Application No. 2015-544188 dated Apr. 26, 2016.

Unofficial English Translation of Japanese Search Report issued in connection with corresponding JP Application No. 2015544188 dated Apr. 28, 2016.

Unofficial English Translation of Japanese Office Action issued in connection with corresponding JP Application No. 2015544188 dated Nov. 15, 2016.

* cited by examiner

METHOD FOR MOVING A MOTORIZED TABLE AND ASSOCIATED MEDICAL IMAGING SYSTEM

CROSS-REFERENCE TO RELATED APPLICATIONS

This is a national stage application under 35 U.S.C. § 371(c) of prior filed, co-pending PCT application serial number PCT/US2013/071938, filed on Nov. 26, 2013, which claims priority to French Patent Application Serial No. 1261298 filed Nov. 27, 2012 and titled METHOD FOR MOVING A MOTORIZED TABLE AND ASSOCIATED MEDICAL IMAGING SYSTEM. All of the above listed applications are herein incorporated by reference.

FIELD OF THE INVENTION

Embodiments of the invention relate to a method for moving a motorized table in a medical imaging system, as well as the associated medical imaging system.

BACKGROUND OF THE INVENTION

In methods for moving medical objects in a medical system, it is sometimes known to have haptic feedback or blockages during certain movements of said medical objects within the medical system. However, this haptic feedback or these movement blockages only occur during the movement of specific objects during particular operating modes of the medical system.

According to a first prior art, for example described in US patent application publication no. US 2009/0253109, a medical driving and learning system is known for controlling a surgical tool offering haptic feedback on the movements by the student using said driving and learning system.

According to a second prior art, for example described in US patent application publication no. US 2007/0129846, an articulated anthropomorphic medical robotic arm is known, whereof certain movements that are not realistic relative to a human arm are inhibited, therefore blocked.

In the two prior arts previously described, nothing even remotely relates to the management of the movement of a motorized table in a medical imaging system, much less with the aim of reducing the dose of radiation received by a patient, part of whose body is being imaged by the medical imaging system.

BRIEF DESCRIPTION OF THE INVENTION

Embodiments of the present invention provide a method for moving a motorized table in a medical imaging system, allowing suitable control of the movements of the motorized table, in particular to avoid having doses of radiation received by a patient in certain parts of his body for which a medical image is not desired or useful. The method for moving a motorized table in a medical imaging system also, in an embodiment, makes it possible to avoid collisions of the equipment around the motorized table and consequently to avoid the disconnection of cables that may be connected to the patient or the medical imaging system. The method for moving a motorized table in a medical imaging system also makes it possible to assist the user of the medical imaging system when that user is driving the movement of motorized table.

In an embodiment, there is provided a method for moving a motorized table in which any movement of the motorized table tending to cause the motorized table to leave a predefined area generates a reaction by the medical imaging system that is perceptible by the user of that medical imaging system. This reaction may be more or less significant and more or less restrictive for the user, depending on the usage mode selected and the desired effect.

To that end, an embodiment of the present invention proposes a method for moving a motorized table designed to receive a patient, in a medical imaging system also comprising a radiation detector capable of detecting a beam of radiation emitted by a radiation source, characterized in that a movement of the motorized table in the plane of the motorized table, causing or tending to cause said beam to at least partially or completely leave an area predefined by the user of the medical imaging system, generates a signal perceptible by said user. The motorized table is driven by the user of the medical imaging system capable of perceiving said signal.

To that end, an embodiment of the present invention also proposes a medical imaging system comprising a motorized table designed to receive a patient, a radiation source, a radiation detector capable of detecting a beam of radiation emitted by said source, characterized in that said medical imaging system also comprises a device able to generate a signal perceptible by the user, in reaction to a movement of the motorized table, in the plane of the motorized table, causing to tending to cause said beam to at least partially or completely leave an area predefined by the user of the medical imaging system.

An embodiment of the invention relates to a method for moving a motorized element driven by a user, in an imaging system also comprising a radiation detector capable of detecting a beam of radiation emitted by a radiation source, characterized in that a movement of the motorized element causing or tending to cause said beam to at least partially or completely leave an area predefined by said user of the imaging system generates a signal perceptible by said user.

An embodiment of the invention also relates to an imaging system comprising a motorized element driven by a user of said imaging system, a radiation source, a radiation detector capable of detecting a beam of the radiation emitted by said source, characterized in that said imaging system also comprises a device capable of generating a signal perceptible by said user, in reaction to a movement of the motorized element, causing or tending to cause said beam to at least partially or completely leave an area predefined by the user of the imaging system.

According to some embodiments, the invention comprises one or more of the following features, which may be used separately, or partially combined with each other, or completely combined with each other.

In an embodiment, said area is defined at the upper surface of the motorized table. In fact, that is where the location closest to the patient is found, which therefore makes it possible to define that area as precisely as possible relative to the patient.

In a first usage mode according to an embodiment, the signal perceptible by said user comprises haptic feedback corresponding to the blockage of said movement so as to prohibit the beam from leaving the predetermined area. This first usage mode offers maximum security, with the drawback, however, of a certain loss of ergonomics. This first usage mode will be reserved for situations where safety issues are crucial, for example when at least one of the connections that risks being disconnected during a relative movement between the motorized table and the rest of the medical imaging system is a connection between the patient and the rest of the medical imaging system. In an embodiment, the patient is connected to the rest of the medical imaging system by at least one or more connections, and, in an embodiment, by at least one connection allowing the injection of an agent into the patient's body designed to improve the contrast of the image done by said detector.

In a second usage mode according to an embodiment, said signal perceptible by the user comprises haptic feedback corresponding to a reduced speed of movement of the motorized table once the beam leaves said predefined area and for the entire time that that beam remains outside the predefined area. The second usage mode offers a good compromise between satisfactory safety and satisfactory ergonomics. The second usage mode will be reserved for situations where safety issues of median importance, for example when the only connections that risk being disconnected during a relative movement between the motorized table and the rest of the medical imaging system are connections between the motorized table and the rest of the medical imaging system. In an embodiment, the patient is not connected to the rest of the medical imaging system by at least one or more connections, and at least one or more cables and/or at least one or more hoses are situated in the field of motion of the motorized table.

In a third user mode according to an embodiment, said signal perceptible by said user comprises a simple alarm, and, in an embodiment, without haptic feedback, emitted at the moment when the beam leaves the predefined area. This third usage mode offers relatively low security, but with good ergonomics. This third usage mode will be reserved for situations where security issues are minimal, for example when no connection risks being disconnected during a relative movement between the motorized table and the rest of the medical imaging system. In an embodiment, said alarm is only emitted when the beam leaves the predefined area. In an embodiment, said alarm is a sound and/or vibrational and/or visual alarm.

All or some of the preceding usage modes may be combined with each other.

In an embodiment, said area may be defined by the user as a trajectory area, i.e. as a corridor that has a given width and that is centered around a trajectory defined by the user. This choice of predefined area is suited to the actual movements that the user will cause the motorized table to undergo in the medical imaging system.

Other features and advantages of the invention will appear upon reading the following description of embodiments of the invention, provided as examples and in reference to the appended drawings.

DETAILED DESCRIPTION OF THE INVENTION

Figure 1:
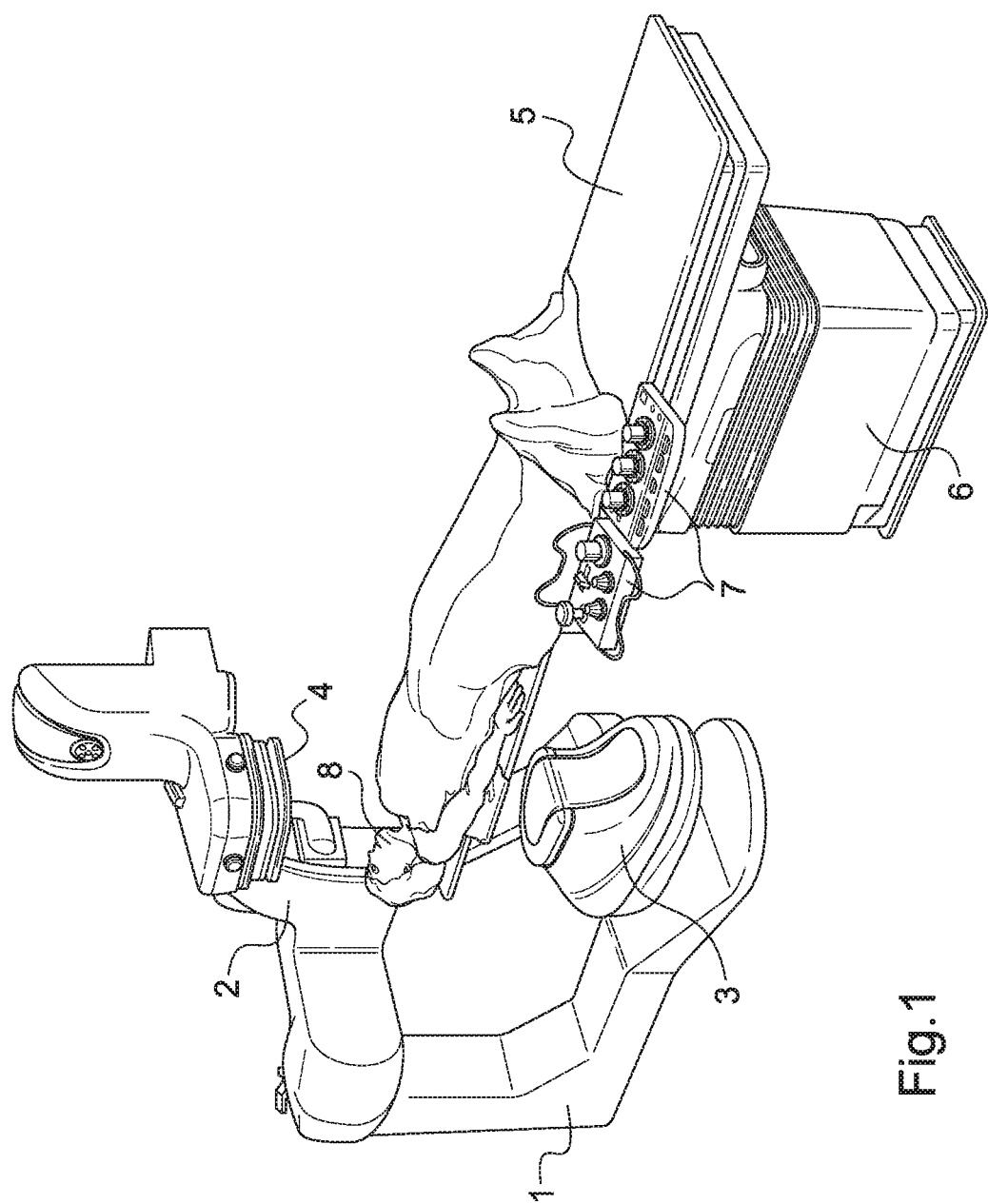
FIG. 1 diagrammatically illustrates a perspective view of one example of a medical imaging system according to one embodiment of the invention.

FIG. 1 diagrammatically shows a perspective view of one example of a medical imaging system according to one embodiment of the invention. The medical imaging system shown in FIG. 1 comprises a self-guided vehicle 1 making it possible to move the medical imaging system and bearing a cradle 2 that is movable relative to the self-guided vehicle 1, for example in rotation. This moving cradle 2 is also called a "C-arm."

The cradle 2 comprises a source of rays 3 at one end, for example a radiation source, for example an x-ray source. The cradle 2 comprises a ray detector 4 at its other end, for example a radiation detector, for example an x-ray detector. The radiation detector 4 can detect a beam of the rays emitted by the radiation source 3.

The medical imaging system also comprises a motorized table 5 designed to receive a patient 8. The motorized table 5 is supported by a base 6 incorporating an articulated arm making it possible to move the motorized table 5. The movement of the motorized table 5 is driven by the user of the medical imaging system by means of a control interface 7.

The medical imaging system also comprises a device capable of generating a signal perceptible by the user, in reaction to a movement of the motorized table 5, in the plane of the motorized table 5, causing or tending to cause the beam of radiation emitted by the source 3 to at least partially or completely leave an area predefined by the user of the medical imaging system by means of the control interface 7.

Figure 2:
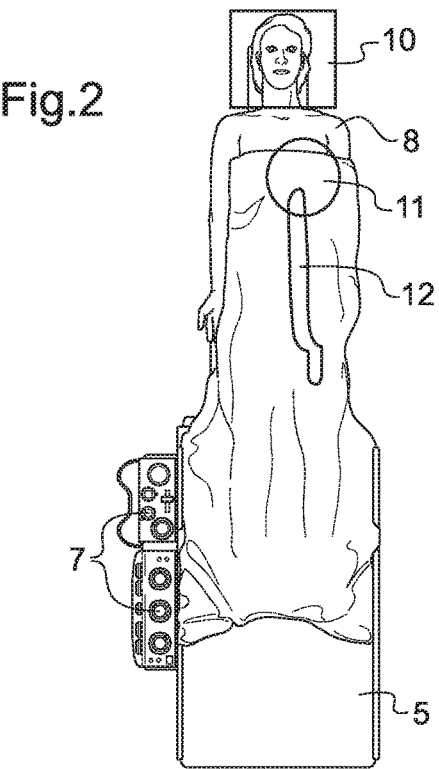
FIG. 2 diagrammatically shows a top view of one example of a medical imaging system according to one embodiment of the invention.

FIG. 2 diagrammatically shows a top view of one example of a medical imaging system according to one embodiment of the invention. Through the control interface 7, the user will define an area outside which the radiation beam emitted by the source 3 is not intended to go. This area, for example the area 10 or the area 11 or the area 12, is defined at the upper surface of the motorized table 5.

There are in particular two ways to define this area. In a first embodiment, this area 12 can be defined by the user as a trajectory area 12, i.e. as a corridor that has a given width and that is centered around a trajectory defined by the user. In a second, optional way, this area 10 or 11 can be defined by the user as a shape area 10 or 11, i.e. as an area 10 or 11 that has a shape defined by the user, for example a square for the area 10 or a circle for the area 11, and which is placed at a location selected by the user, for example at the head of the patient 8 for the area 10 or at the heart of the patient 8 for the area 11.

When a movement of the motorized table 5, in the plane of the motorized table 5, causes or tends to cause the radiation beam emitted by the source 3 to at least partially or completely leave the area defined by the user of the medical imaging system, whether it is the area 10 or the area 11 or the area 12 depending on the case, the medical imaging system generates a signal perceptible by the user, such that the user realizes that the radiation beam emitted by the source 3 has left its defined area 10 or 11 or 12 in which it was intended to remain.

Figure 3:
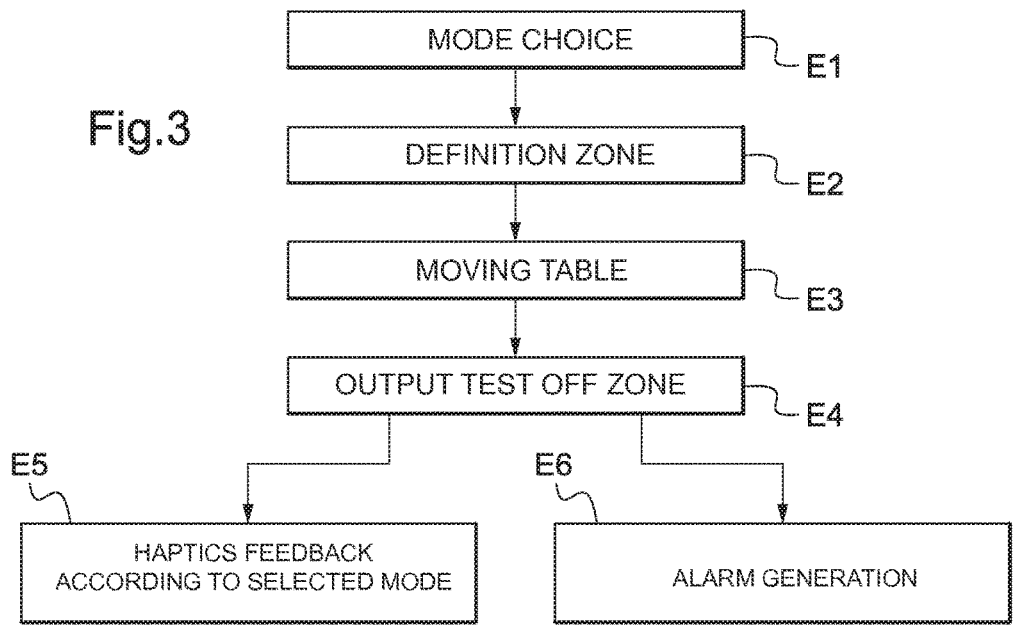
FIG. 3 diagrammatically shows one example of the progression of the steps of a method for moving a motorized table in a medical imaging system according to one embodiment of the invention.

FIG. 3 diagrammatically shows an example of the progression of the steps of a method for moving a motorized table in a medical imaging system according to one embodiment of the invention. The user first chooses a usage mode in step E1, which determines the type of reaction of the medical imaging system in response to an attempt by the beam to leave the area that will be defined in step two. Then, the user defines an area in step E2, which is the area inside which the radiation beam emitted by the source is intended to remain. Then, during step E3, the user commands the movement(s) of the motorized table on which a patient has been positioned.

During step E3, if the motorized table remains within the defined area, nothing happens. During this step E3, if the motorized table leaves or tends to leave the predefined area, the method advances to step E4, where that departure or attempted departure is diagnosed by the medical imaging system. In reaction to that departure or attempted departure, the medical imaging system reacts either by a step E5, in which haptic feedback is generated so as to be received by the user, the type of haptic feedback being related to the user mode chosen by the user during step E1, or step E6, in which an alarm is generated in the event the corresponding usage mode was chosen by the user during step E1.

Step E5 will now be described in more detail. Step E5 is used in particular when the patient is connected to the rest of the medical imaging system by at least one or more connections, and, in an embodiment, by at least one connection allowing the injection of an agent into the patient's body designed to improve the contrast of the image done by the detector. In that case, the signal perceptible by the user comprises haptic feedback corresponding to the blockage of the movement commanded by the user so as to prohibit the beam from leaving the defined area. The haptic feedback is often force feedback, giving the user the sensation that he has encountered a hindrance or an obstacle, for example such as an abrupt blockage of the remote-control handle giving the sensation of an impact against a stationary obstacle. This step E5 is also used in particular when the patient is not connected to the rest of the medical imaging system by at least one or more connections, and when at least one or more cables and/or one or more hoses are situated in the field of movement of the motorized table. In that case, the signal perceptible by the user comprises haptic feedback corresponding to a reduction in the speed of movement of the motorized table once the beam leaves the predefined area and for the entire time that the beam remains outside that predefined area.

Step E6 will now be described in more detail. Step E6 is in particular used when no connection risks being disconnected during the movement of the motorized table. In that case, the signal perceptible by the user comprises a simple alarm with no haptic feedback emitted when the beam leaves the predefined area. This alarm is only emitted when the beam leaves the predefined area. This alarm therefore does not continue to be emitted if the beam remains outside the predefined area. This alarm may for example be a sound and/or vibrational and/or visual alarm.

Of course, the present invention is not limited to the examples and embodiments described and shown, but rather is open to many alternatives accessible to those skilled in the art.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for moving a motorized table associated with a medical imaging system comprising:
    setting a predefined area relative to a surface of the motorized table within which a beam of radiation from a radiation source is intended to remain;
    effectuating one or more movements of the motorize table; and
    generating a signal if any of the one or more movements of the motorized table will cause the beam of radiation to at least partially leave the predefined area, the signal being perceptible by a user of the medical imaging system.

2. The method for moving a motorized table according to claim 1, wherein said area is defined at an upper surface of the motorized table.

3. The method for moving a motorized table according to claim 1, wherein the signal comprises haptic feedback corresponding to the blockage of said one or more movements so as to prohibit the beam of radiation from leaving the predefined area.

4. The method for moving a motorized table according to claim 1, wherein said signal is an audible, visible and or/vibrational signal.

5. The method for moving a motorized table according to claim 1, wherein said area is defined by the user as a trajectory area.

6. The method for moving a motorized table according to claim 5, wherein the trajectory area is a corridor having a given width and is centered around a trajectory defined by the user.

7. The method for moving a motorized table according to claim 1, wherein said area is defined by the user as a shape area.

8. The method for moving a motorized table according to claim 7, wherein the shape area has a shape defined by the user and is placed at a location selected by the user.

9. A medical imaging system, comprising:
    a motorized table defining a surface configured to support a patient;
    a radiation source;
    a radiation detector configured to detect a beam of radiation emitted by said radiation source;
    a control interface to enable a user to set an predefined area relative to the surface of the motorized table within which the radiation beam is intended to remain during imaging; and
    a device configured to generate a visual, audible or vibrational alert when any of one or more movements of the motorized table effectuated by a user of the medical imaging system will cause the beam of radiation to at least partially leave the predefined area.

10. A medical imaging system, comprising:
    a movable table;
    a radiation source to emit a radiation beam;
    a device configured to generate a signal in reaction to an input to effectuate a movement of the table which will cause the radiation beam to at least partially leave a predefined area within which the radiation beam is intended to be constrained;
    a perceptible alert activated by the signal which indicates that the input to effectuate a movement of the table will cause the radiation beam to at least partially leave the predefined are; and
    a control device that prevents movements of the motorized table upon receiving the signal to prevent the beam from completely or at partially leaving the predefined area.

11. The medical imaging device of claim 10, wherein the alert is a visual, audible and/or vibrational alarm.

\* \* \* \* \*